United States Patent

Takaya et al.

Patent Number: 4,590,186
Date of Patent: May 20, 1986

[54] CEPHEM COMPOUNDS HAVING 3-BICYCLIC HETEROCYCLIC CATION GROUPS

[75] Inventors: Takao Takaya; Kazuo Sakane, both of Kawanishi; Hideaki Yamanaka, Hirakata, all of Japan

[73] Assignee: Fujisawa Pharmaceutical Co., Ltd., Osaka, Japan

[21] Appl. No.: 690,251

[22] Filed: Jan. 10, 1985

[30] Foreign Application Priority Data

Jan. 16, 1984 [GB] United Kingdom ............... 8401093

[51] Int. Cl.⁴ ............... A61K 31/545; C07D 501/46
[52] U.S. Cl. ............... 514/202; 544/22; 544/237; 544/235; 548/356; 548/369
[58] Field of Search ............... 544/22; 514/202

[56] References Cited

U.S. PATENT DOCUMENTS 4,366,153 12/1982 Takaya ............... 544/27
4,396,620 8/1983 Lunn ............... 544/22
4,525,473 6/1985 Aburaki ............... 514/202

FOREIGN PATENT DOCUMENTS 0062321 10/1982 European Pat. Off. ............ 514/202
2098216 5/1981 United Kingdom ............... 514/202

Primary Examiner—Donald G. Daus
Assistant Examiner—Robert Benson

Attorney, Agent, or Firm—Oblon, Fisher, Spivak, McClelland & Maier

[57] ABSTRACT

The invention relates to cephem compounds of high antimicrobial activity of the formula:

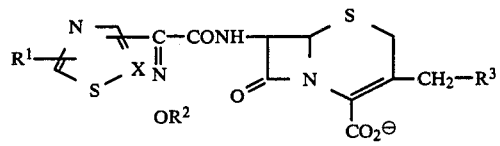

wherein
$R^1$ is amino or protected amino,
$R^2$ is lower aliphatic hydrocarbon group,
$R^3$ is a group of the formula:

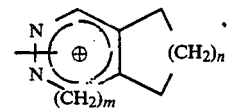

wherein
m is 0 and or 1, and
n is 1 or 2,
which may have a lower alkyl substituent at the N atom, and
X is CH or N,
and pharmaceutically acceptable salts thereof.

6 Claims, No Drawings

CEPHEM COMPOUNDS HAVING 3-BICYCLIC HETEROCYCLIC CATION GROUPS

The present invention relates to new cephem compounds and pharmaceutically acceptable salts thereof. More particularly, it relates to new cephem compounds and pharmaceutically acceptable salts thereof, which have antimicrobial activities and to a process for preparation thereof, to pharmaceutical composition comprising the same, and to a method of using the same therapeutically in the treatment of infectious diseases in human being and animals.

Accordingly, it is one object of the present invention to provide new cephem compounds and pharmaceutically acceptable salts thereof, which are active against a number of pathogenic microorganisms.

Another object of the present invention is to provide a process for the preparation of new cephem compounds and pharmaceutically acceptable salts thereof.

A further object of the present invention is to provide pharmaceutical composition comprising, as active ingredients, said new cephem compounds and pharmaceutically acceptable salts thereof.

Still further object of the present invention is to provide a method for the treatment of infectious diseases caused by pathogenic bacteria in human being and animals.

The object new cephem compounds are novel and can be represented by the following general formula (I).

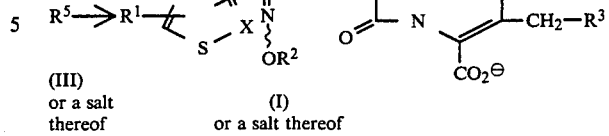

wherein
R$^1$ is amino or protected amino,
R$^2$ is lower aliphatic hydrocarbon group,
R$^3$ is unsaturated condensed heterocyclic cation group containing more than one nitrogen atom, which may have suitable substituent(s), and
X is CH or N.

According to the present invention, the new cephem compounds (I) can be prepared by the process which is illustrated in the following scheme.

Process

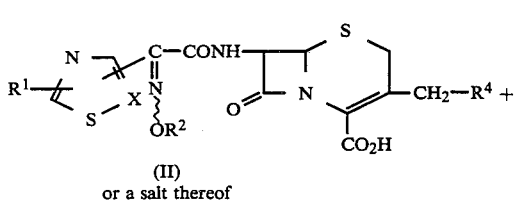

(II)
or a salt thereof

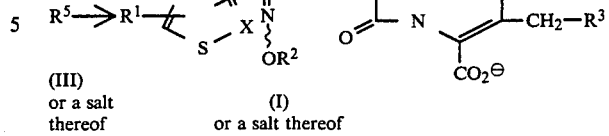

(III)
or a salt thereof (I)
or a salt thereof wherein
R$^1$, R$^2$, R$^3$ and X are each as defined above,
R$^4$ is a group which can be substituted by a group R$^3$, and
R$^5$ is unsaturated condensed heterocyclic compound containing more than one nitrogen atom, which may have suitable substituent(s).

Regarding the object compound (I) and the starting compound (II), it is to be understood that said object and starting compounds include syn isomer, anti isomer and a mixture thereof. For example, with regard to the object compound (I), syn isomer means one geometrical isomer having the partial structure represented by the following formula:

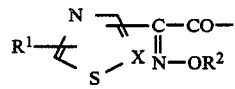

(wherein R$^1$, R$^2$ and X are each as defined above) and anti isomer means the other geometrical isomer having the partial structure represented by the following formula:

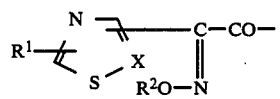

(wherein R$^1$, R$^2$ and X are each as defined above).

Regarding the starting compound (II), as mentioned above, the syn isomer and the anti isomer can also be, referred to the same geometrical isomers as illustrated for the compound (I).

Suitable pharmaceutically acceptable salts of the object compound (I) are conventional non-toxic salt and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, maleate, tartrate, methanesulfonate, benzenesulfonate, formate, toluenesulfonate, etc.), an inorganic acid salt (e.g. hydrochloride, hydrobromide, hydroiodide, sulfate, phosphate, etc.), or a salt with an amino acid (e.g. arginine, aspartic acid, glutamic acid, etc.), and the like.

In the above and subsequent descriptions of the present specification, suitable examples and illustrations of the various definitions which the present invention include within the scope thereof are explained in detail as follows.

The term "lower" is intended to mean 1 to 6 carbon atom(s) unless otherwise indicated.

Suitable "protected amino" for R$^1$ may include an acylamino or an amino group substituted by a conventional protecting group such as ar(lower)alkyl which may have suitable substituent(s) (e.g. benzyl, trityl, etc.) or the like.

Suitable acyl moiety in the terms "acylamino" and "acyloxy" may include carbamoyl, aliphatic acyl group and acyl group containing an aromatic or heterocyclic ring. And, suitable examples of the said acyl may be lower alkanoyl (e.g. formyl, acetyl, propionyl, butyryl, isobutyryl, valeryl, isovaleryl, oxalyl, succinyl, pivaloyl, etc.);

lower alkoxycarbonyl (e.g. methoxycarbonyl, ethoxycarbonyl, propoxycarbonyl, 1-cyclopropylethoxycarbonyl, isopropoxycarbonyl, butoxycarbonyl, tertiarybutoxycarbonyl, pentyloxycarbonyl, hexyloxycarbonyl, etc.); lower alkanesulfonyl (e.g. mesyl, ethanesulfonyl, propanesulfonyl, isopropanesulfonyl, butanesulfonyl, etc.);

arenesulfonyl (e.g. benzenesulfonyl, tosyl, etc.); aroyl (e.g. benzoyl, toluoyl, xyloyl, naphthoyl, phthaloyl, indancarbonyl, etc.); ar(lower)alkanoyl (e.g. phenylacetyl, phenylpropionyl, etc.);

ar(lower)alkoxycarbonyl (e.g. benzyloxycarbonyl, phenethyloxycarbonyl, etc.), and the like. The acyl moiety as stated above may have suitable substituent(s) such as acyl (e.g. lower alkanoyl), halogen (e.g. chlorine, bromine, iodine or fluorine) or the like.

Suitable lower aliphatic hydrocarbon group may include lower alkyl, lower alkenyl, lower alkynyl and the like.

Suitable "lower alkyl" is one having 1 to 6 carbon atom(s) and may include methyl, ethyl, propyl, isopropyl, butyl, isobutyl, tert-butyl, pentyl, tertpentyl, hexyl and the like, and preferably one having 1 to 4 carbon atom(s).

Suitable "lower alkenyl" is one having 2 to 6 carbon atoms and may include vinyl, allyl, isopropenyl, 1-propenyl, 2-butenyl, 3-pentenyl and the like, and preferably one having 2 to 4 carbon atoms.

Suitable "lower alkynyl" is one having 2 to 6 carbon atoms and may include ethynyl, 2-propynyl, 2-butynyl, 3-pentynyl, 3-hexynyl and the like, and preferably one having 2 to 4 carbon atoms.

Suitable $R^4$ may include an acid residue such as acyloxy, halogen (e.g. chlorine, bromine, iodine or fluorine), azido or the like, wherein acyl moiety in the term "acyloxy" can be referred to the ones as exemplified above.

Suitable unsaturated condensed heterocyclic cation group containing more than one nitrogen atom for $R^3$ may be a group of the formula:

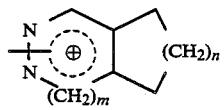

wherein
m is 0 or 1, and
n is 1 or 2.

Suitable examples of said $R^3$ may include
5,6-dihydro-1H,4H-cyclopenta[c]pyrazolio,
5,6-dihydro-2H,4H-cyclopenta[c]pyrazolio,
5,6-dihydro-3H,4H-cyclopenta[c]pyrazolio,
4,5,6,7-tetrahydro-1H-indazolio,
4,5,6,7-tetrahydro-2H-indazolio,
4,5,6,7-tetrahydro-3H-indazolio,
5,6,7,8-tetrahydrophthalazinio and the like.

Suitable unsaturated condensed heterocyclic compound containing more than one nitrogen atom for $R^5$ may be a compound of the formula:

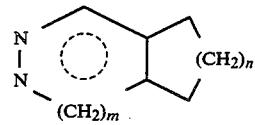

wherein m and n are each as defined above.

Suitable examples of said $R^5$ may include
5,6-dihydro-1H,4H-cyclopenta[c]pyrazole,
5,6-dihydro-2H,4H-cyclopenta[c]pyrazole,
5,6-dihydro-3H,4H-cyclopenta[c]pyrazole,
4,5,6,7-tetrahydro-1H-indazole,
4,5,6,7-tetrahydro-2H-indazole,
4,5,6,7-tetrahydro-3H-indazole,
5,6,7,8-tetrahydrophthalazine and the like.

Both of said unsaturated condensed heterocyclic cation group containing more than one nitrogen atom and said unsaturated condensed heterocyclic compound containing more than one nitrogen atom may have suitable substituent(s) such as lower alkyl (e.g. methyl, ethyl, propyl, isopropyl, butyl, pentyl, hexyl, etc.) or the like.

Preferred embodiments of the object compounds (I) are as follows.

Preferred embodiment of $R^1$ is amino.

Preferred embodiment of $R^2$ is lower alkyl or lower alkenyl.

Preferred embodiment of $R^3$ is a group of the formula:

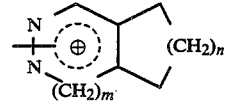

(wherein m and n are each as defined above), more preferably, 5,6-dihydro-1H,4H-cyclopenta[c]pyrazolio, 4,5,6,7-tetrahydro-1H-indazolio, 4,5,6,7-tetrahydro-2H-indazolio and 5,6,7,8-tetrahydrophthalazinio, each of which may have lower alkyl.

The process for preparing the object compounds of the present invention is explained in detail in the following.

Process

The object compound (I) or a salt thereof can be prepared by reacting the compound (II) or a salt thereof with the compound (III) or a salt thereof.

Suitable salt of the compound (II) can be referred to the ones as exemplified for the compound (I).

Suitable salt of the compound (III) can be referred to the acid addition salt as exemplified for the compound (I).

The present reaction may be carried out in a solvent such as water, phosphate buffer, acetone, chloroform, acetonitrile, nitrobenzene, methylene chloride, ethylene chloride, formamide, dimethylformamide, alcohol (e.g. methanol, ethanol, etc.), ether, tetrahydrofuran, dimethylsulfoxide, or any other organic solvent which does not adversely affect the reaction, preferably in ones having strong polarities. Among the solvents, hydrophilic solvents may be used in a mixture with water.

The reaction is preferably carried out in around neutral medium. When the compound (II) is used in a free form, the reaction is preferably conducted in the presence of a base, for example, inorganic base such as alkali metal hydroxide, alkali metal carbonate, alkali metal bicarbonate, organic base such as trialkylamine, and the like.

The reaction temperature is not critical, and the reaction is usually carried out at ambient temperature, under warming or under heating.

The present reaction is preferably carried out in the presence of alkali metal halide (e.g. sodium iodide, potassium iodide, etc.), alkali metal thiocyanate (e.g. sodium thiocyanate, potassium thiocyanate, etc.) etc.

The object compounds (I) of the present invention exhibit high antimicrobial activity and inhibit the growth of a number of microorganisms including pathogenic Gram-positive and Gram-negative bacteria.

For therapeutic administration, the cephalosporin compounds according to the present invention are used in the form of pharmaceutical preparation which contain said compounds in admixture with a pharmaceutically acceptable carriers such as an organic or inorganic solid or liquid excipient suitable for oral, parenteral or external administration. The pharmaceutical preparations may be in solid form such as capsule, tablet, dragee, ointment or suppository, or in liquid form such as solution, suspension, or emulsion. If desired, there may be included in the above preparations auxiliary substances, stabilizing agents, wetting or emulsifying agents, buffers and other commonly used additives.

While the dosage of the compounds may vary from and also depend upon the age and condition of the patient, an average single dose of about 50 mg., 100 mg., 250 mg., and 500 mg. of the compounds according to the present invention may be effective for treating of infectious diseases caused by a number of pathogenic bacteria. In general amounts, daily dose between 1 mg/body and about 1000 mg/body or even more may be administered.

Now in order to show the utility of the object compounds (I), test data on anti-microbial activity of representative compounds of the present invention are shown below.

Test Method

One loopful of an overnight culture of each test strain in Trypticase-soy broth ($10^8$ viable cells per ml) was streaked on heart infusion agar (HI-agar) containing graded concentrations of antibiotics, and the minimal inhibitory concentration (MIC) was expressed in terms of µg/ml after incubation at 37° C. for 20 hours.

Test Compounds (1) 7-[2-Methoxyimino-2-(2-aminothiazol-4-yl)-acetamido]-3-[1-methyl-5,6-dihydro-2(1H,4H)-cyclopenta[c]pyrazolio]methyl-3-cephem-4-carboxylate (syn isomer)

(2) 7-[2-Methoxyimino-2-(2-aminothiazol-4-yl)-acetamido]-3-[1-methyl-4,5,6,7-tetrahydro-2(1H)-indazolio]methyl-3-cephem-4-carboxylate (syn isomer)

Test Results

| | M.I.C. (µg/ml) | |
|---|---|---|
| | Test compounds | |
| Test bacteria | (1) | (2) |
| E. coli 35 | 0.050 | 0.050 |
| K. pneumoniae 12 | 0.100 | 0.100 |

The following examples are given for the purpose of illustrating the present invention.

EXAMPLE 1

A mixture of sodium 7-[2-allyloxyimino-2-(5-amino-1,2,4-thiadiazole-3-yl)acetamido]-3-acetoxymethyl-3-cephem-4-carboxylate (syn isomer)(6.43 g), 1-methyl-5,6-dihydro-1H,4H-cyclopenta[c]pyrazole (3.2 g), sodium iodide (20.54 g), phosphoric acid (0.67 g), water (2.8 ml) and acetonitrile (8.5 ml) was stirred at 70° to 75° C. for 2 hours. The reaction mixture was poured into water (100 ml) and the aqueous layer was adjusted to pH 2.0 with 10% hydrochloric acid. After removal of precipitates by filtration, the aqueous solution was washed with ethyl acetate four times. The aqueous layer was adjusted to pH 2.5 with 5% aqueous solution of sodium bicarbonate and subjected to column chromatography on macroporous non-ionic adsorption resin Diaion HP-20 (Trademark : prepared by Mitsubishi Chemical Industries). The column was washed with water and eluted with 50% aqueous methanol. The fractions containing the object compound were combined and methanol was evaporated under reduced pressure. The resultant aqueous solution was lyophilized to give 7-[2-allyloxyimino-2-(5-amino-1,2,4-thiadiazol-3-yl)-acetamido]-3-[1-methyl-5,6-dihydro-2(1H,4H)-cyclopenta[c]pyrazolio]methyl-3-cephem-4-carboxylate (syn isomer)(1.3 g).

IR (Nujol) : 3300, 1770, 1668, 1630, 1605 cm$^{-1}$.

NMR (D$_2$O, δ) : 2.5-3.0 (6H, m), 3.35 (2H, br.s), 3.96 (3H, s), 4.8 (2H, m), 5.30 (1H, d, J=5Hz), 5.1-5.5 (2H, m), 5.93 (1H, d, J=5Hz), 6.0 (1H, m), 7.84 (1H, s).

EXAMPLE 2

The following compounds were obtained according to a similar manner to that of Example 1.

(1) 7-[2-Ethoxyimino-2-(5-amino-1,2,4-thiadiazol-3-yl)acetamido]-3-[1-methyl-5,6-dihydro-2(1H,4H)-cyclopenta[c]pyrazolio]methyl-3-cephem-4-carboxylate (syn isomer).

IR (Nujol) : 3300, 1773, 1668, 1610 cm$^{-1}$.

NMR (D$_2$O, β) : 1.33 (3H, t, J=7Hz), 2.8 (6H, m), 3.32 (2H, m), 3.93 (3H, s), 4.36 (2H, q, J=7Hz), 5.26 (1H, d, J=5Hz), 5.30 (2H, m), 5.88 (1H, d, J=5Hz), 7.78 (6H, s).

(2) 7-[2-Allyloxyimino-2-(2-aminothiazol-4-yl)-acetamido]-3-[1-methyl-5,6-dihydro-2(1H,4H)-cyclopenta[c]pyrazolio]methyl-3-cephem-4-carboxylate (syn isomer).

IR (Nujol) : 3270, 1772, 1660, 1607 cm$^{-1}$.

NMR (D$_2$O, δ) : 2.80 (6H, m), 3.33 (2H, m), 3.90 (3H, s), 4.80 (2H, m), 5.28 (1H, d, J=5Hz), 5.38 (2H, m), 6.96 (1H, s), 7.75 (1H, s).

(3) 7-[2-Methoxyimino-2-(2-aminothiazol-4-yl)acetamido]-3-[1-methyl-5,6-dihydro-2(1H,4H)cyclopenta[c]pyrazolio]methyl-3-cephem-4-carboxylate (syn isomer).

IR (Nujol) : 3290, 1770, 1662, 1608 cm$^{-1}$.

NMR (D₂O, δ): 2.63 (6H, m), 3.28 (2H, m), 3.87 (3H, s), 3.93 (3H, s), 5.18 (1H, d, J=5Hz), 5.23 (2H, m), 5.78 (1H, d, J=5Hz), 6.90 (1H, s), 7.75 (1H, s).

(4) 7-[2-Allyloxyimino-2-(5-amino-1,2,4-thiadiazol-3-yl)acetamido]-3-[1-methyl-4,5,6,7-tetrahydro-2(1H)indazolio]methyl-3-cephem-4-carboxylate (syn isomer).

IR (Nujol): 3250, 1765, 1653, 1600 cm⁻¹.

NMR (D₂O-acetone-d₆, δ): 1.73 (4H, m), 2.50 3.23 (2H, m), 3.80 (3H, s), 5.26 (1H, d, J=5Hz), 5.4 (2H, m), 5.93 (1H, d, J=5Hz), 6.0 (1H, m), 7.98 (1H, s).

(5) 7-[2-Allyloxyimino-2-(5-amino-1,2,4-thiadiazol-3-yl)acetamido]-3-[2-methyl-4,5,6,7-tetrahydro-1(2H)-indazolio]methyl-3-cephem-4-carboxylate (syn isomer).

IR (Nujol): 3300, 1770, 1672, 1610 cm⁻¹.

NMR (D₂O-acetone-d₆, δ): 1.84 (4H, m), 2.56 (2H, m), 2.88 (2H, m), 3.04,3.40 (2H, ABq, J=16Hz), 4.16 (3H, s), 4.76 (2H, d, J=6Hz), 5.20 (1H, d, J=5Hz), 5.24, 5.52 (2H, ABq, J=8Hz), 5.92 (1H, d, J=5Hz), 6.00 (1H, m), 8.04 (1H, s).

(6) 7-[2-Ethoxyimino-2-(5-amino-1,2,4-thiadiazol-3-yl)acetamido]-3-[1-methyl-4,5,6,7-tetrahydro-2(1H)-indazolio]methyl-3-cephem-4-carboxylate (syn isomer).

IR (Nujol): 3300, 1765, 1668, 1607 cm⁻¹.

NMR (D₂O, δ): 1.33 (3H, t, J=7Hz), 1.80 (4H, m), 2.60 (4H, m), 3.30 (2H, m), 3.87 (3H, s), 4.33 (2H, q, J=7Hz), 5.25 (1H, d, J=5Hz), 5.37 (2H, m), 5.89 (1H, d, J=5Hz), 7.92 (1H, s).

(7) 7-[2-Methoxyimino-2-(2-aminothiazol-4-yl)acetamido]-3-[1-methyl-4,5,6,7-tetrahydro-2(1H)indazolio]methyl-3-cephem-4-carboxylate (syn isomer).

IR (Nujol): 3300, 1772, 1668, 1610 cm⁻¹.

NMR (D₂O-acetone-d₆, δ): 1.80 (2H, m), 2.60 (4H, m), 3.28 (2H, m), 3.83 (3H, s), 4.00 (3H, s), 5.20 (1H, d, J=5Hz), 5.30 (2H, m), 5.82 (1H, d, J=5Hz), 6.93 (1H, s), 7.90 (1H, s).

(8) 7-[2-Ethoxyimino-2-(5-amino-1,2,4-thiadiazol-3-yl)acetamido]-3-(5,6,7,8-tetrahydro-2-phthalazinio)-methyl-3-cephem-4-carboxylate (syn isomer).

IR (Nujol): 3300, 1777, 1663, 1610 cm⁻¹.

NMR (D₂O-acetone-d₆, δ): 1.30 (3H, t, J=7Hz), 1.90 (4H, m), 3.05 (4H, m), 3.63 (2H, m), 4.30 (2H, q, J=7Hz), 5.25 (1H, d, J=5Hz), 5.58 (2H, m), 5.83 (1H, d, J=5Hz), 9.05 (1H, s), 9.53 (1H, s).

(9) 7-[2-Methoxyimino-2-(2-aminothiazol-4-yl)acetamido]-3-(5,6,7,8-tetrahydro-2-phthalazinio)methyl3-cephem-4-carboxylate (syn isomer).

IR (Nujol): 3300, 1775, 1660, 1610 cm⁻¹.

NMR (D₂O-acetone-d₆, δ): 1.90 (4H, m), 3.03 (4H, m), 3.63 (2H, m), 4.0 (3H, s), 5.23 (1H, d, J=5Hz), 5.60 (2H, m), 5.83 (1H, d, J=5Hz), 6.87 (1H, s), 9.08 (1H, s), 9.53 (1H, s).

What we claim is:

1. A cephem compound of the formula:

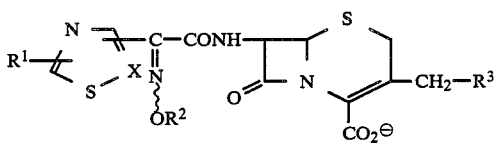

wherein
R¹ is amino or protected amino,
R² is lower aliphatic hydrocarbon group,
R³ is a group of the formula:

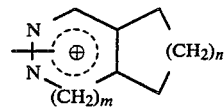

wherein
m is 0 or 1, and
n is 1 or 2,
which may have a lower alkyl substituent at the N atom, and
X is CH or N,
and pharmaceutically acceptable salts thereof.

2. A syn isomer of the compound of claim 1, wherein

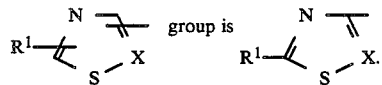

3. A compound of claim 2, wherein
R¹ is amino, and
R² is lower alkyl or lower alkenyl.

4. A compound of claim 3, wherein
R² is methyl, ethyl or allyl, and
R³ is 5,6-dihydro-1H,4H-cyclopenta[c]pyrazolio, 4,5,6,7-tetrahydro-1H-indazolio, 4,5,6,7-tetrahydro-2H-indazolio or 5,6,7,8-tetrahydrophthalazinio, each of which may have methyl.

5. A compound of claim 4, which is selected from the compound consisting of:
7-[2-allyloxyimino-2-(5-amino-1,2,4-thiadiazol-3-yl)acetamido]-3-[1-methyl-5,6-dihydro-2(1H,4H)cyclopenta[c]pyrazolio]methyl-3-cephem-4-carboxylate(syn isomer),
7-[2-ethoxyimino-2-(5-amino-1,2,4-thiadiazol-3-yl)acetamido]-3-[1-methyl-5,6-dihydro-2(1H,4H)cyclopenta[c]pyrazolio]methyl-3-cephem-4-carboxylate (syn isomer),
7-[2-allyloxyimino-2-(2-aminothiazol-4-yl)acetamido]-3-[1-methyl-5,6-dihydro-2(1H,4H)-cyclopenta[c]pyrazolio]methyl-3-cephem-4-carboxylate (syn isomer),
7-[2-methoxyimino-2-(2-aminothiazol-4-yl)acetamido]-3-[1-methyl-5,6-dihydro-2(1H,4H)-cyclopenta[c]pyrazolio]methyl-3-cephem-4-carboxylate (syn isomer),
7-[2-allyloxyimino-2-(5-amino-1,2,4-thiadiazol-3-yl)acetamido]-3-[1-methyl-4,5,6,7-tetrahydro-2(1H)-indazolio]methyl-3-cephem-4-carboxylate (syn isomer),
7-[2-allyloxyimino-2-(5-amino-1,2,4-thiadiazol-3-yl)acetamido]-3-[2-methyl-4,5,6,7-tetrahydro-1(2H)indazolio]methyl-3-cephem-4-carboxylate (syn isomer),
7-[2-ethoxyimino-2-(5-amino-1,2,4-thiadiazol-3-yl)acetamido]-3-[1-methyl-4,5,6,7-tetrahydro-2(1H)indazolio]methyl-3-cephem-4-carboxylate (syn isomer),
7-[2-methoxyimino-2-(2-aminothiazol-4-yl)acetamido]-3-[1-methyl-4,5,6,7-tetrahydro-2(1H)-indazolio]methyl-3-cephem-4-carboxylate (syn isomer),
7-[2-ethoxyimino-2-(5-amino-1,2,4-thiadiazol-3-yl)acetamido]-3-(5,6,7,8-tetrahydro-2-phthalazinio)-methyl-3-cephem-4-carboxylate (syn isomer) and
7-[2-methoxyimino-2-(2-aminothiazol-4-yl)acetamido]-3-(5,6,7,8-tetrahydro-2-phthalazinio)methyl-3-cephem-4-carboxylate (syn isomer).

6. A pharmaceutically antimicrobial composition comprising an antimicrorally effective amount of compound of claim 1 or a pharmaceutically acceptable salt thereof as an effective ingredient, in association with a pharmaceutically acceptable, substantially non-toxic carrier or excipient.

* * * * *